US012649057B2

(12) United States Patent
    Colachis et al.

(10) Patent No.: US 12,649,057 B2
(45) Date of Patent: Jun. 9, 2026

(54) FINITE ELEMENT MODEL OF CURRENT DENSITY AND ELECTRICAL IMPEDANCE TOMOGRAPHY BASED METHOD FOR FUNCTIONAL ELECTRICAL STIMULATION

(71) Applicant: Battelle Memorial Institute, Columbus, OH (US)

(72) Inventors: Sam Colachis, Columbus, OH (US); David Friedenberg, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 708 days.

(21) Appl. No.: 18/018,453

(22) PCT Filed: Jul. 30, 2021

(86) PCT No.: PCT/US2021/043942
    § 371 (c)(1),
    (2) Date: Jan. 27, 2023

(87) PCT Pub. No.: WO2022/026854
    PCT Pub. Date: Feb. 3, 2022

(65) Prior Publication Data
    US 2023/0285750 A1      Sep. 14, 2023

Related U.S. Application Data

(60) Provisional application No. 63/058,977, filed on Jul. 30, 2020, provisional application No. 63/058,968, filed on Jul. 30, 2020.

(51) Int. Cl.
    *A61N 1/36*      (2006.01)
    *A61B 5/0536*    (2021.01)
    *A61N 1/04*      (2006.01)

(52) U.S. Cl.
    CPC ........ *A61N 1/36003* (2013.01); *A61B 5/0536* (2013.01); *A61N 1/0484* (2013.01); *A61N 1/36034* (2017.08)

(58) Field of Classification Search
    CPC ............ A61N 1/36003; A61N 1/36034; A61B 5/0536
    (Continued)

(56) References Cited

U.S. PATENT DOCUMENTS

2008/0154340 A1      6/2008  Goetz et al.
2010/0004715 A1      1/2010  Fahey
    (Continued)

FOREIGN PATENT DOCUMENTS

WO        2020/112986 A1     6/2020

*Primary Examiner* — Nadia A Mahmood
(74) *Attorney, Agent, or Firm* — VOLPE KOENIG

(57) ABSTRACT

Systems and methods for generating a finite element model (FEM) of current flow in an anatomical human forearm are disclosed. The disclosed FEM may assist in determining optimal stimulation parameters in electrical stimulation systems for achieving movement of paralyzed limbs or enhancement of able limbs. This model will allow users to determine which muscle groups are receiving stimulation under different parameters. Systems and methods which leverage electrical impedance tomography (EIT) for autonomous recalibration following garment donning are also disclosed. The method may comprise performing an EIT measurement across an electrode array of an electrode garment and constructing an anatomical model based on the EIT measurement. Next, one or more alignment variations may be estimated based on an alignment variation model. Finally, the electrode array is adjusted, automatically or manually, to accommodate the alignment variations using an alignment adjustment function.

20 Claims, 9 Drawing Sheets

(58) Field of Classification Search
USPC ........................................................ 607/48
See application file for complete search history.

(56) References Cited

U.S. PATENT DOCUMENTS

| | | | |
|---|---|---|---|
| 2015/0038823 A1 | 2/2015 | Brunner et al. | |
| 2016/0055304 A1 | 2/2016 | Russell et al. | |
| 2016/0228702 A1 | 8/2016 | Kempe et al. | |
| 2017/0105678 A1 | 4/2017 | Xue | |
| 2017/0296059 A1 | 10/2017 | Anderson | |
| 2018/0146881 A1 | 5/2018 | Garber | |
| 2018/0154133 A1 | 6/2018 | Bouton et al. | |
| 2018/0200514 A1* | 7/2018 | Druke | A61B 5/6832 |
| 2019/0255325 A1 | 8/2019 | John et al. | |
| 2020/0353239 A1 | 11/2020 | Daniels | |
| 2020/0406035 A1 | 12/2020 | Sharm | |
| 2021/0353942 A1 | 11/2021 | Friedenberg | |

* cited by examiner 100
101
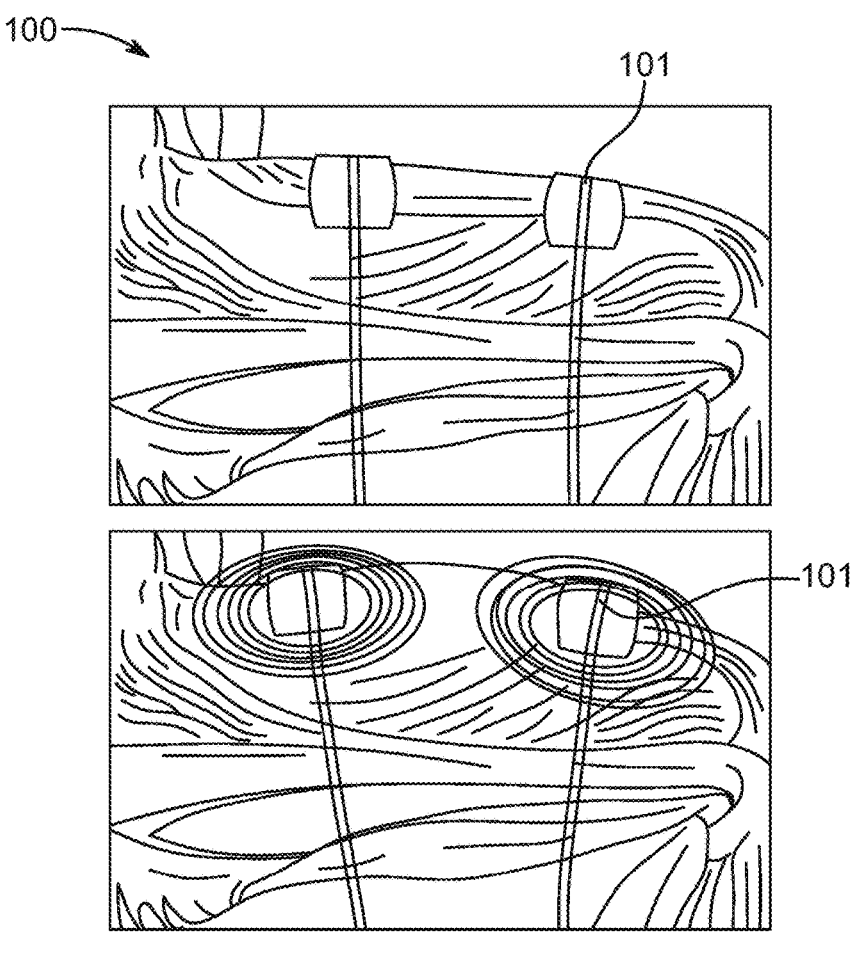
FIG. 1
200
201
203
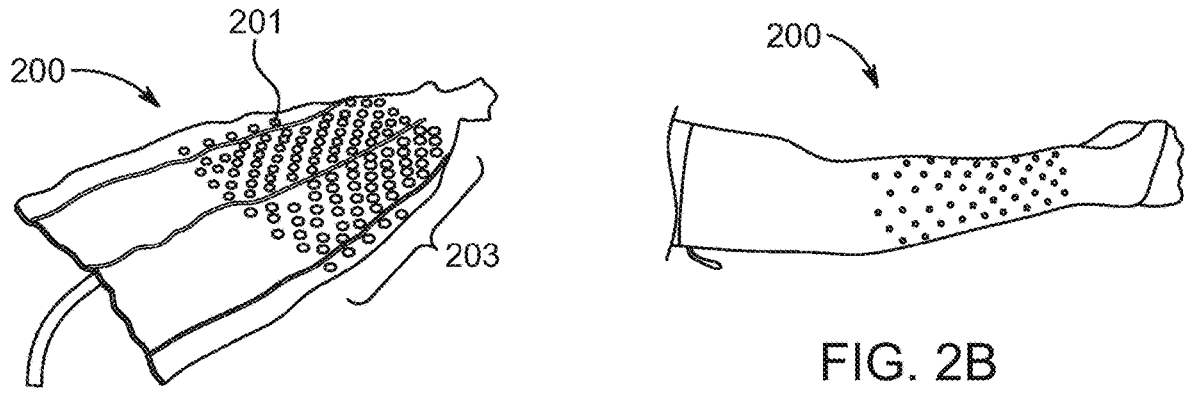
FIG. 2A
200
FIG. 2B

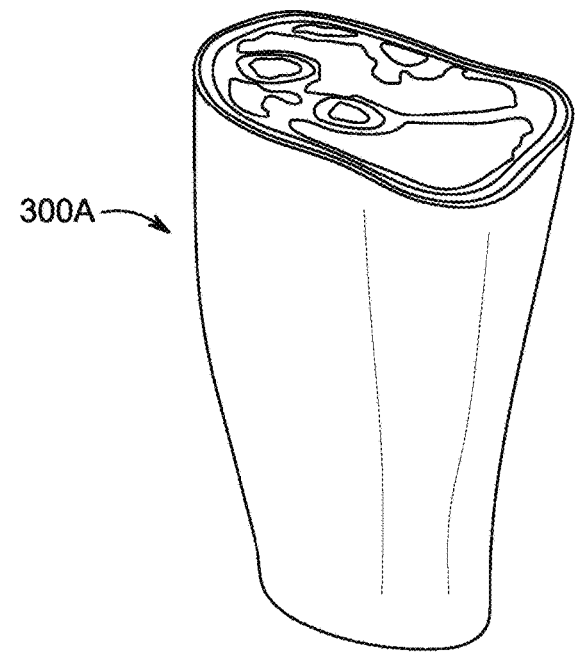
300A
FIG. 3A
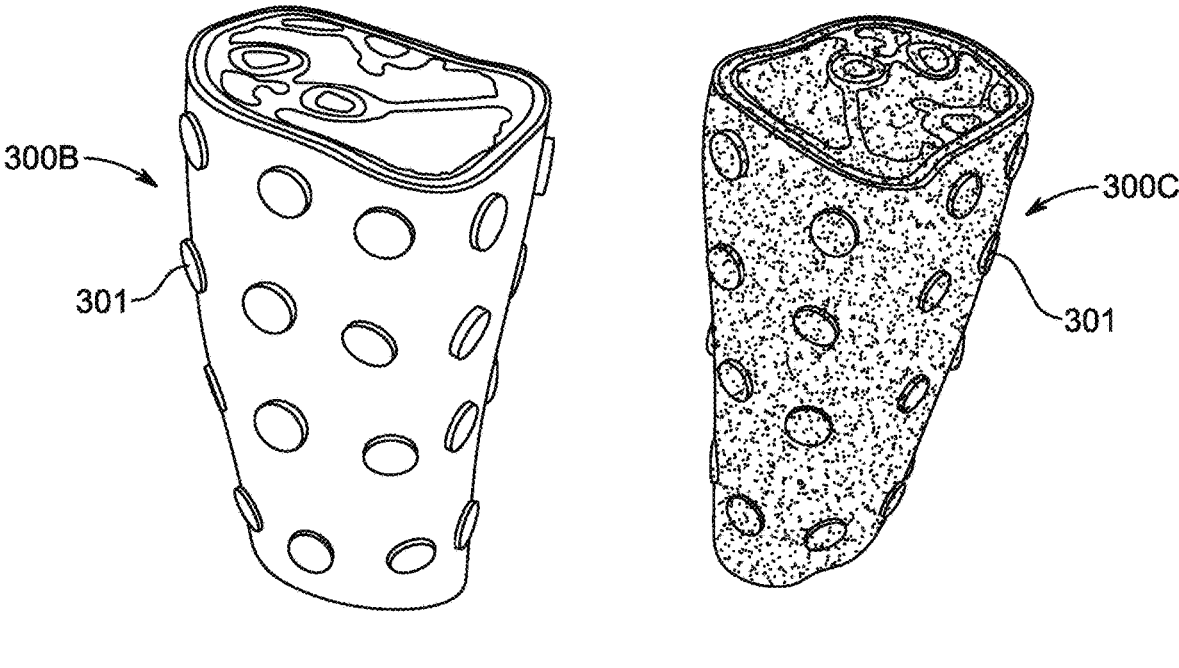
300B
301
FIG. 3B
300C
301
FIG. 3C

700

950

FINITE ELEMENT MODEL OF CURRENT DENSITY AND ELECTRICAL IMPEDANCE TOMOGRAPHY BASED METHOD FOR FUNCTIONAL ELECTRICAL STIMULATION

CROSS REFERENCE TO RELATED APPLICATIONS

This application claims the benefit of U.S. Provisional No. 63/058,968, filed on Jul. 30, 2020, and U.S. Provisional No. 63/058,977, filed on Jul. 30, 2020, which are incorporated by reference as if fully set forth.

FIELD OF INVENTION

The invention relates generally to neuromuscular electrical stimulation (NMES). More particularly, the invention relates to models for predicting muscle activation during NMES.

BACKGROUND

Limb paralysis is a common outcome of a spinal cord injury or stroke. Individuals with limb paralysis have hindered hand movement, making activities of daily living difficult to impossible. Neuromuscular electrical stimulation (NMES) uses electrical impulses to induce muscular contractions. Specifically, NMES comprises delivering electrical pulses via electrodes, through skeletal muscles, to activate a motor response. Muscle fibers in skeletal muscles respond to electrical signals sent through motor neurons. NMES induces a foreign electrical current which overrides the natural motor neuron activity and causes a muscle contraction. This may reanimate muscular movement in paralyzed limbs. NMES may also be used to enhance able limbs, for example, in sports performance enhancement and therapy. Functional electrical stimulation (FES) is a subset of NMES which focuses on promoting functional movement.

Electromyography (EMG) is a diagnostic test that measures how well the muscles respond to the electrical signals emitted to specialized nerve cells called motor nerves.

A garment comprising an array of electrodes embedded therein may be configured for NMES, EMG, or both NMES and EMG. For example, the NeuroLife® group at the Battelle Memorial Institute has developed a high density electrode NMES/EMG sleeve which both excites muscle and records muscle excitation and has a variety of applications. For example, the NeuroLife® sleeve may allow tetraplegic individuals to regain functional hand movements. The NeuroLife® sleeve may also be used as a component in a closed-loop system for rehab for stroke, spinal cord injury, multiple sclerosis, amyotrophic lateral sclerosis, or any other injuries that disrupt normal hand/arm function.

However, a high density electrode NMES device, such as the NeuroLife® sleeve, may comprise as many as 160 electrodes. Currently, electrode patterns of electrode garments for generating movement are chosen using a trial and error process by which electrodes are added and removed until a desired movement is achieved. This is very time and labor intensive. Further, the trial and error method may pose difficulties in optimizing stimulation parameters since it is not known which muscles are being activated during each stimulation pattern. A model of current flow in an anatomical human forearm would assist in the determination of optimal NMES/EMG parameters.

Further, FES and/or EMG garments are susceptible to inter-session and inter-subject variability in electrode positioning during the donning process. Garment alignment inconsistencies and anatomical differences between subjects and/or users may affect system calibrations, such as FES patterns used to evoke movement. If the garment position is shifted, a corresponding shift in active electrodes may be required to compensate for the misalignment. Furthermore, anatomical differences between subjects and/or users may require de novo pattern calibration. Calibration may be achieved through trial and error where an operator manually selects individual electrodes for discrete activation and then iteratively refines the pattern. Not only is this process tedious and inefficient, but the discrete states of electrodes may impose a coarse resolution that make fine adjustments difficult. Therefore, a method for autonomous recalibration following garment donning would be extremely useful in the areas of NMES and EMG.

SUMMARY

Systems and methods for generating a finite element model (FEM) of current flow in an anatomical human forearm are disclosed. The disclosed FEM may assist in determining optimal stimulation parameters in electrical stimulation systems for achieving movement of paralyzed limbs or enhancement of able limbs. This model may enable users to determine which muscle groups are receiving stimulation under different parameters.

Systems and methods which leverage electrical impedance tomography (EIT) for autonomous recalibration following garment donning are also disclosed. The method may comprise performing an EIT measurement across an electrode array of an electrode garment and constructing an anatomical model based on the EIT measurement. Next, one or more alignment variations may be estimated based on an alignment variation model. Finally, the electrode array is adjusted, automatically or manually, to accommodate the alignment variations using an alignment adjustment function.

BRIEF DESCRIPTION OF THE DRAWINGS

FIG. 1 is a diagram illustrating a representative NMES treatment;

FIG. 2A is an image of an NMES/EMG sleeve, according to an embodiment;

FIG. 2B is an image of the NMES/EMG sleeve of FIG. 2A as worn by a subject, according to an embodiment;

FIG. 3A is perspective view of an anatomical model of a forearm, according to an embodiment;

FIG. 3B is the anatomical model of FIG. 3A comprising electrodes, according to an embodiment;

FIG. 3C is a mesh of the anatomical model of FIGS. 3A and 3B, according to an embodiment;

DETAILED DESCRIPTION OF THE PREFERRED EMBODIMENTS

Figure 4A:
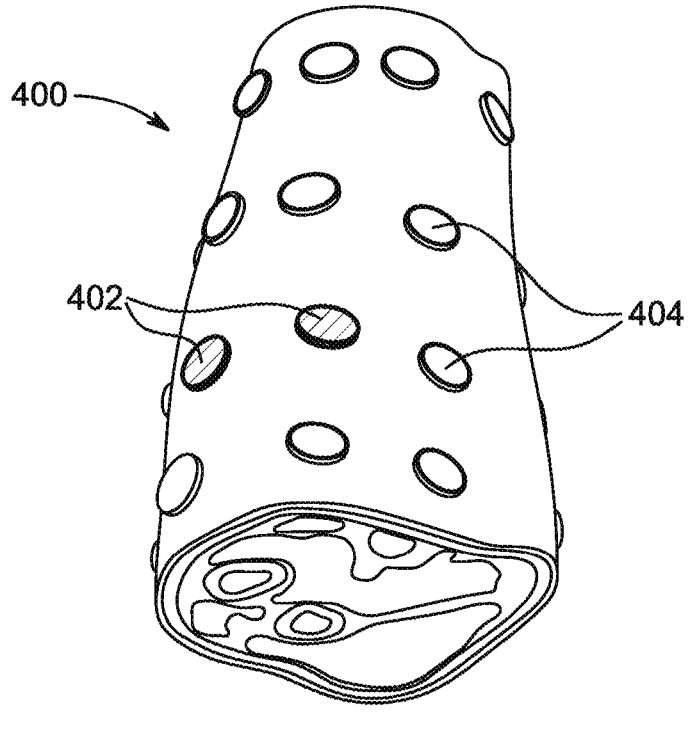
FIG. 4A is a perspective view of the anatomical model with active anodes for targeting flexor muscle, according to an embodiment.

Systems and methods for generating a finite element model (FEM) of current flow in an anatomical human forearm are disclosed. The disclosed FEM may assist in determining optimal stimulation parameters to achieve movement of paralyzed limbs. This model will allow users to determine which muscle groups are receiving stimulation for different electrode patterns and parameters. Although this disclosure is discussed with respect to an anatomical model of the forearm, as persons having ordinary skill in the art will appreciate, this model may be applicable to other limbs of the human body.

Systems and methods leveraging electrical impedance tomography (EIT) to adjust electrode-based recording and/ or stimulation calibrations that are dependent on electrode placement are also disclosed. These methods may be applied to garments designed for neuromuscular electrical stimulation (NMES) and/or electromyography (EMG) to ensure consistent electrode alignment and provide a method for autonomous recalibration. However, as will be appreciated by one having ordinary skill in the art, this method may be applied to any electrode-based recording and/or stimulation calibrations which are dependent upon electrode placement.

FIG. 1 is a diagram illustrating a representative NMES treatment 100. NMES comprises delivering electrical pulses via electrodes to skeletal muscles in order to activate a motor response. Muscle fibers in skeletal muscles respond to electrical signals sent through motor neurons. NMES induces a foreign electrical current which overrides the natural motor neuron activity and causes a muscle contraction. This is beneficial for individuals with impaired neuronal connections, such as spinal cord injury or stroke patients. NMES may be used to achieve movement of paralyzed limbs. NMES may also be used to enhance movement of able limbs, for example, in sports performance enhancement and therapy. Functional electrical stimulation (FES) is a subset of NMES which focuses on promoting functional movement. In FIG. 1, electrodes 101 are placed on a subject's skin and activated, delivering electrical impulses to skeletal muscles and thereby causing a muscle contraction.

A garment comprising an array of electrodes embedded therein may be configured to provide NMES treatments.

FIG. 2A is a NMES/EMG sleeve 200 in an open position, according to an embodiment. FIG. 2B is an image of the NMES/EMG sleeve 200 as worn by a subject, according to an embodiment. The NMES/EMG sleeve 200 may comprise an array 203 of high density electrodes 201 which contact the skin of a subject to stimulate one or more muscles in the forearm and to record muscle activity. In some embodiments, a conductive medium, such as a hydrogel, may be placed between the electrode and the skin. In some embodiments, the electrodes 201 are relatively small to allow for fine motor control. In some embodiments, the NMES sleeve 200 may comprise as many as 160 electrodes 201. Each electrode 201 of the array of electrodes 203 may comprise an anode or a cathode.

Each electrode 201 of the array of electrodes 203 may be configured to be inactive or active. The active electrodes may be configured to be an anode (i.e., generate current) or to be a cathode (i.e., receive current). As used herein, the term "pattern" refers to the specific configuration of active and inactive electrodes, as well as the amplitude and waveform of each electrode.

Alternative devices for electrical stimulation include subcutaneous implantable neurostimulation devices. These implantable devices are wrapped around a target nerve and generally include one or more electrodes arranged to stimulate the nerve. By including more than one electrode and/or a different geometry of electrodes, implantable devices such as the flat interface nerve electrode (FINE) have been able to achieve stimulation selectivity at the level of individual nerve vesicles.

FIG. 3A is an anatomical model of a forearm 300A, according to an embodiment. Medical imaging techniques, such as magnetic resonance imaging (MRI) and computed tomography (CT), may be used to obtain scans of a limb. EIT may be used to obtain a scan of a limb. EIT is a noninvasive type of imaging in which the electrical conductivity of a part of the body is inferred from surface electrode measurements and used to form a tomographic image of that part. Specifically, EIT uses an array of surface electrodes and high frequency alternating current (AC) to measure internal electrical impedance. By placing an array of electrodes around a body part, it is possible to reconstruct the internal impedance distribution and infer the internal structure. For example, EIT measurements may be used to generate an anatomical model of a limb of interest and identify locations of rigid anatomical markers, such as bone.

Scans obtained using MRI, CT, and/or EIT may then be processed using three-dimensional (3D) image segmentation software, such as ScanIP. In some embodiments, grayscale values may be used to isolate skin, fat, connective tissue, muscles, bone and bone marrow. Each of these tissue types may be treated as homogeneous materials. Conductivity values for the tissue types found in the model may be known or previously measured. For example, previous studies may report the conductivity values for the tissue types found in the model. These conductivity values may be applied to the associated materials in the FEM. Table 1 is an example of material properties for skin, fat, connective tissue, muscle, bone (cortical), and bone marrow (yellow). The segmented materials may be combined to create the anatomical model of the forearm 300A.

TABLE 1

| Material | Electrical Conductivity (S/m) | Relative Permittivity |
|---|---|---|
| Skin | 0.491 | 1 |
| Fat | 0.0684 | 1 |
| Connective Tissue | 0.49 | 1 |
| Muscle | 0.708 | 1 |
| Bone (cortical) | 0.0643 | 1 |
| Bone Marrow (yellow) | 0.0232 | 1 |

Referring to FIG. 3B, electrodes 301 may be modeled on the anatomical model 300B. In some embodiments, the electrodes 301 of the anatomical model may mirror the placement of electrodes of the electrical stimulation device. In some embodiments, the electrodes 301 may be physically modeled as a circular disk with stainless steel material properties. However, as will be appreciated by one having ordinary skill in the art, the electrodes 301 may be physically modeled as having different shapes and/or different material properties. Further, in some embodiments, the electrodes 301 may be anchored flush to the skin surface of the model. In some embodiments, a conductive medium, such as a hydrogel may be placed between the electrode and the skin of the model. In alternative embodiments, the electrodes may be implanted in the anatomical model to mimic the effects of a subcutaneous implantable neurostimulation device. The electrodes 301 may form an array of electrodes, as illustrated in FIG. 3B.

Each electrode 301 of the array of electrodes may be configured to be inactive or active. The active electrodes are configured to either be an anode (i.e., generate current) or to be a cathode (i.e., receive current). As used herein, the term "pattern" refers to the specific configuration of active and inactive electrodes, as well as the amplitude and waveform of each electrode.

Referring to FIG. 3C, a mesh of the anatomical model of the forearm 300C and electrodes 301 may be generated. As used herein, the term "mesh" refers to a collection of vertices, edges and faces that defines the shape of the anatomical model. In some embodiments, the resulting mesh is a FEM.

Once an anatomical model is generated, such as those illustrated in FIGS. 3A-3C, current density analyses may be performed. The current density analyses may be performed using a multi-physics package, such as COMSOL Multiphysics®. In COMSOL Multiphysics®, the FEM may use the Electrical Current interface. In some embodiments, a stationary study may be used.

The electrical current may be modeled in the multi-physics package using the Maxwell's Continuity Equations (Equations 1-3).

$$-\nabla * (\sigma \nabla V) = -\frac{\partial \rho_v}{\partial t} \qquad \text{Eq. 1}$$

$$E = -\nabla V \qquad \text{Eq. 2}$$

$$J = \sigma E \qquad \text{Eq. 3}$$

In equations 1-3, $\sigma$ represents the conductivity of the tissue and electrodes, V represents the voltage, $\rho$ represents the charge density, E represents the electric field, and J represents the electric current density.

The active anodes of the FEM may be assigned voltage boundaries. Similarly, the active cathodes may be assigned current source boundary. These settings may correspond to the maximum allowed current the system is capable of. By way of example only, the active anodes may be assigned voltage boundaries conditions of 200 V and the active cathodes may be assigned current source boundary conditions of −20 mA. In some embodiments, all the other boundaries in the FEM are electrically insulated.

Figure 4B:
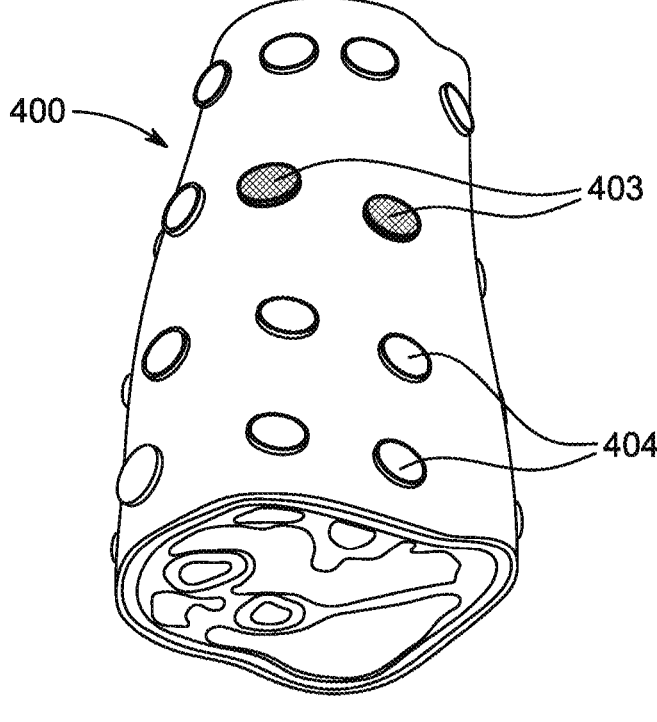
FIG. 4B is a perspective view of the anatomical model with active cathodes for targeting flexor muscle, according to an embodiment.

Referring to FIGS. 4A and 4B, for each electrode pattern of interest, specific electrodes may be modeled to generate or receive current (i.e., be a cathode or anode, respectively). FIG. 4A illustrates an anatomical model of a forearm 400 with the location of active anodes 402 for targeting flexor muscle of the forearm. FIG. 4B shows the anatomical model 400 location of active cathodes 403 for targeting flexor muscle of the forearm. Inactive electrodes 404 may be included in the mesh, as illustrated in FIGS. 4A and 4B.

Current density through the FEM may be visualized at all depths. Therefore, the FEM may be used to run simulations to determine where current is flowing for a particular pattern. In this way, the FEM may be used to determine which muscle current is flowing to (i.e., which muscle is activated) for a particular pattern. For example, FIGS. 5A-5C, described in more detail below, illustrate current flow during the targeted flexor stimulation shown in FIGS. 4A and 4B.

Figure 5A:
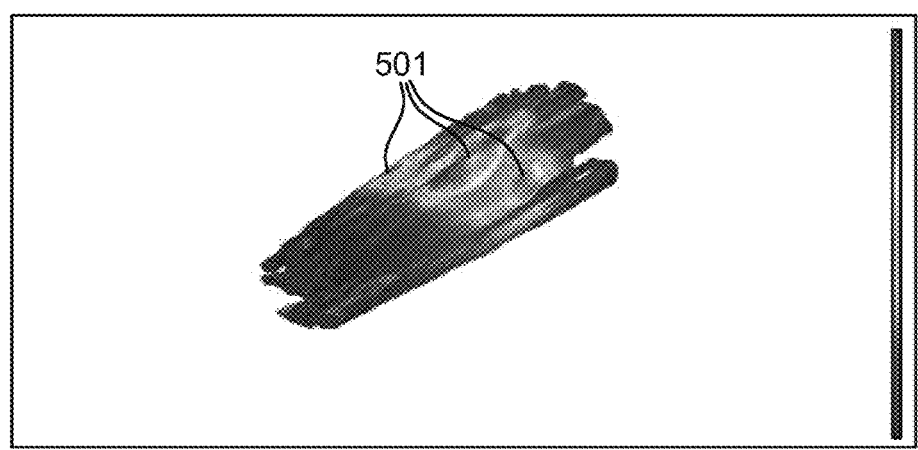
FIG. 5A is a perspective view of the anatomical model showing current density on the forearm muscles during targeted flexor stimulation, according to an embodiment.
Figure 5B:
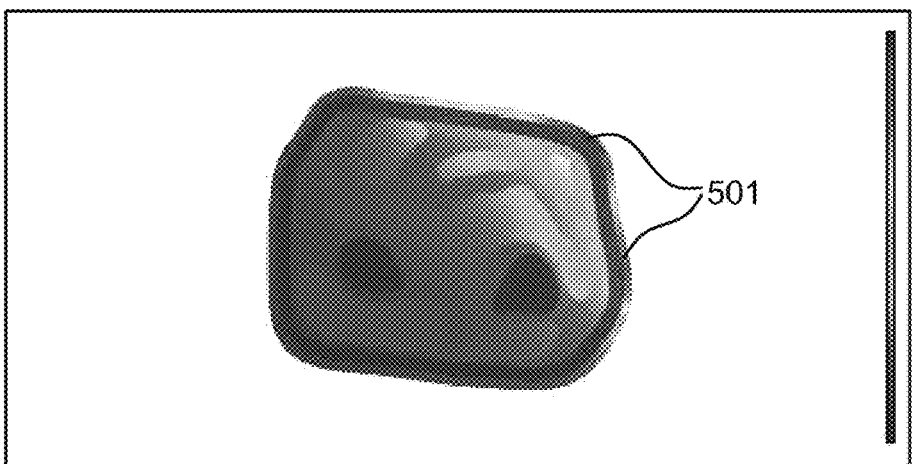
FIG. 5B is a slice view of the anatomical model showing current density through tissue during targeted flexor stimulation, according to an embodiment.
Figure 5C:
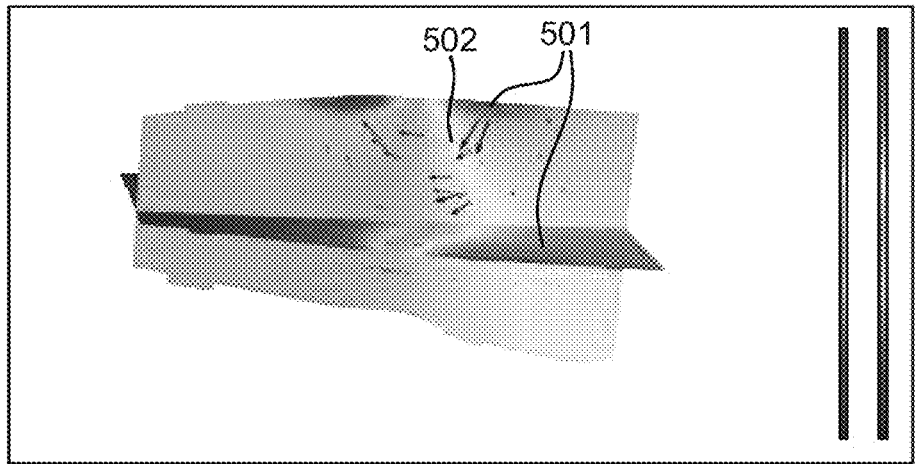
FIG. 5C is a view of the coronal and sagittal planes of the anatomical model showing electrical potential and current flow, according to an embodiment.

FIG. 5A is a perspective view of the anatomic model showing current density on the forearm muscles during targeted flexor stimulation, according to an embodiment. FIG. 5B is a slice view of the anatomical model showing current density through tissue during targeted flexor stimulation, according to an embodiment. FIG. 5C is a view of the coronal and sagittal planes of the forearm model showing electrical potential during targeted flexor stimulation, according to an embodiment. The current density illustrated in FIGS. 5A-5C represents the current density when the electrodes are arranged as shown in FIGS. 4A and 4B.

In FIGS. 5A-5C, the forearm muscle which receives the highest amount of current density is shown as 501. The arrows 502 in FIG. 5C represent anode to cathode current flow through the forearm during targeted flexor stimulation.

In addition to current localization, current density at varying amplitudes may also be determined using the disclosed FEM model. In some embodiments, current density through tissue may be determined using the FEM model when the cathode current source is set to different amplitudes.

Figure 6A:
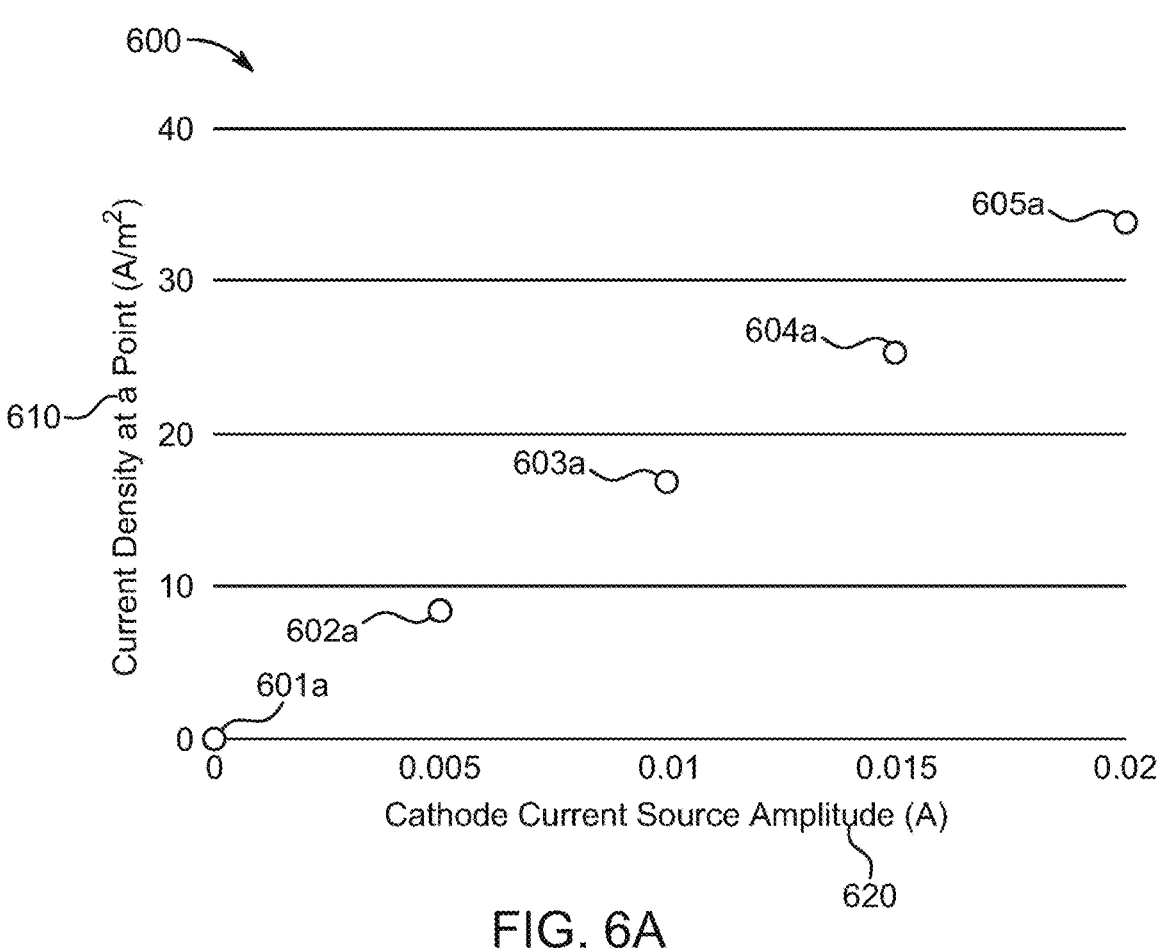
FIG. 6A is a graph showing the current density for various amplitudes of when the cathode current source is set to various amplitudes, according to an embodiment.

FIG. 6A is a graph 600 illustrating current density 610 when the cathode current source is set to various amplitudes 620. Specifically, at 601a, 602a, 603a, 604a, and 605a, the cathode current source is set to an amplitude of 0, 0.005, 0.010, 0.015, and 0.020, respectively.

Figure 6B:
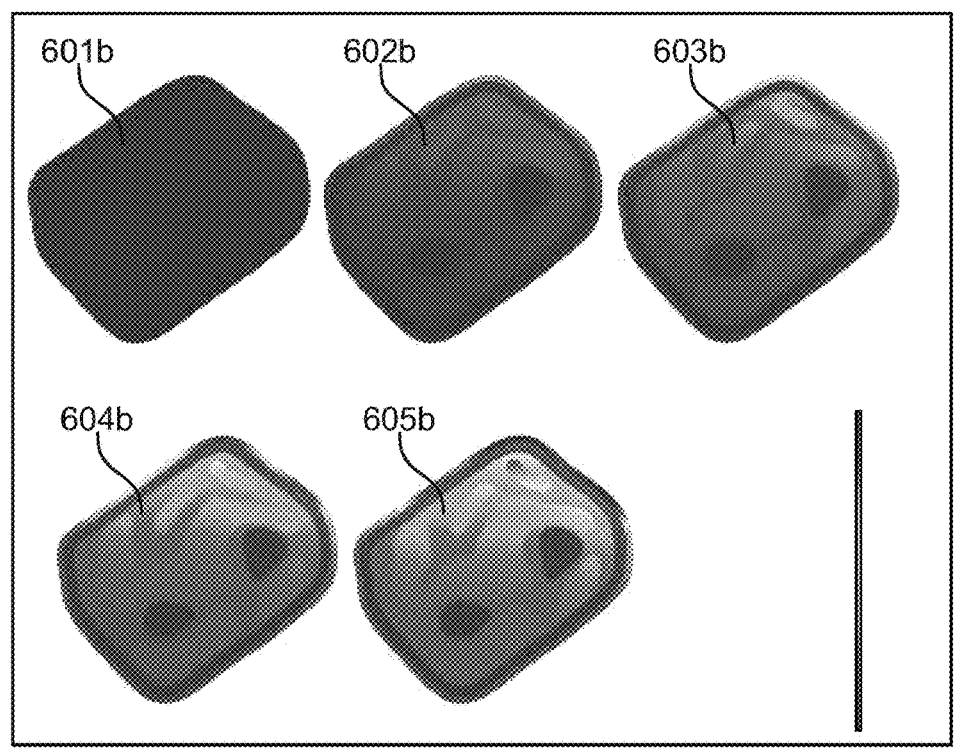
FIG. 6B illustrates slice views of the anatomical model showing current density when the cathode source is set to various amplitudes during targeted flexor stimulation, according to an embodiment.

FIG. 6B illustrates slice views of the anatomical model showing current density of through tissue during targeted flexor stimulation. Specifically, slice views 601b, 602b, 603b, 604b, and 605b illustrate the current density through tissue at amplitudes of 0, 0.005, 0.010, 0.015, and 0.020, respectively.

Figure 7:
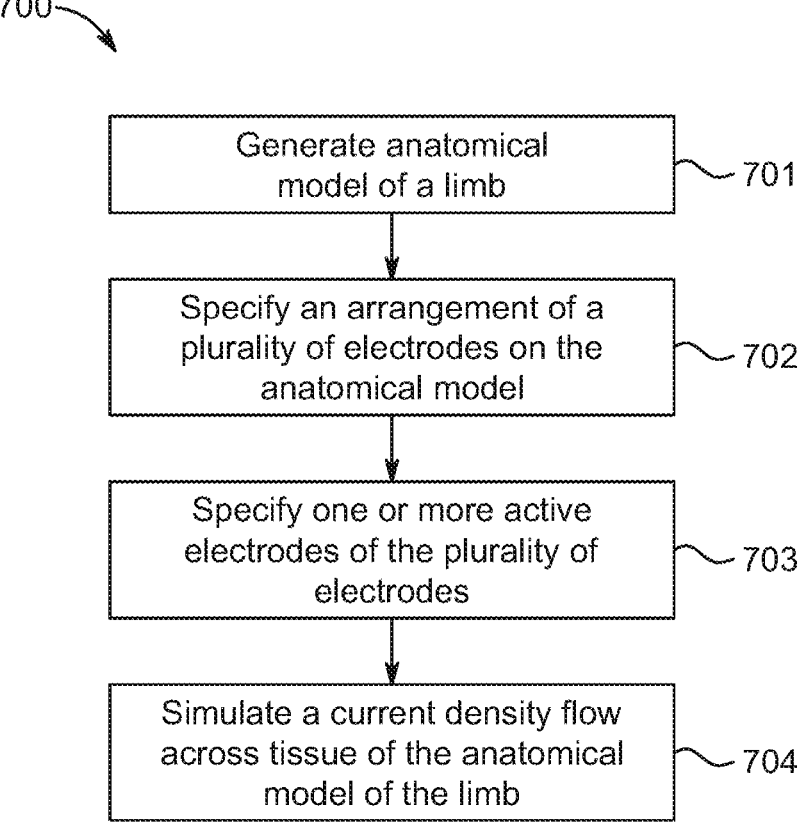
FIG. 7 is a flowchart diagram of a method for modeling current density flow during NMES, according to an embodiment.

FIG. 7 is a flowchart diagram of a method for modeling current density flow during NMES 700, in accordance with the embodiments disclosed above. At 701, an anatomical model of a limb is generated. The method of FIG. 7 may be performed by a processor. In some embodiments, the anatomical model is a FEM, as discussed above. Next, at 702, an arrangement of a plurality of electrodes is specified on or in the anatomic model. In some embodiments, the arrangement of the plurality of electrodes may be selected to reflect the array of electrodes of the NMES/EMG device. In alternate embodiments, In some embodiments, the electrodes may be implanted in the anatomical model to mimic the effects of a subcutaneous implantable neurostimulation device. One or more active electrodes of the plurality of electrodes are specified at 703. Finally, at 704, a current density flow is simulated across tissue of the anatomical model.

These simulations may be used to determine the most accurate and effective pattern of electrodes for activating a target muscle. This may be done manually, or through an algorithm. In some embodiments, the most accurate and effective electrode pattern is determined using a numerical optimization algorithm that determines a plurality of stimulation patterns for an array of electrodes. In some embodiments, the numerical optimization algorithm is a differential evolution algorithm. In other embodiments, the numerical optimization algorithm is a Bayesian operation. In some embodiments, a target muscle may be tagged to track current density, as illustrated in FIGS. 6A and 6B, and a pattern that output the most localized current density for the target muscle may be output from the algorithm.

Figure 8:
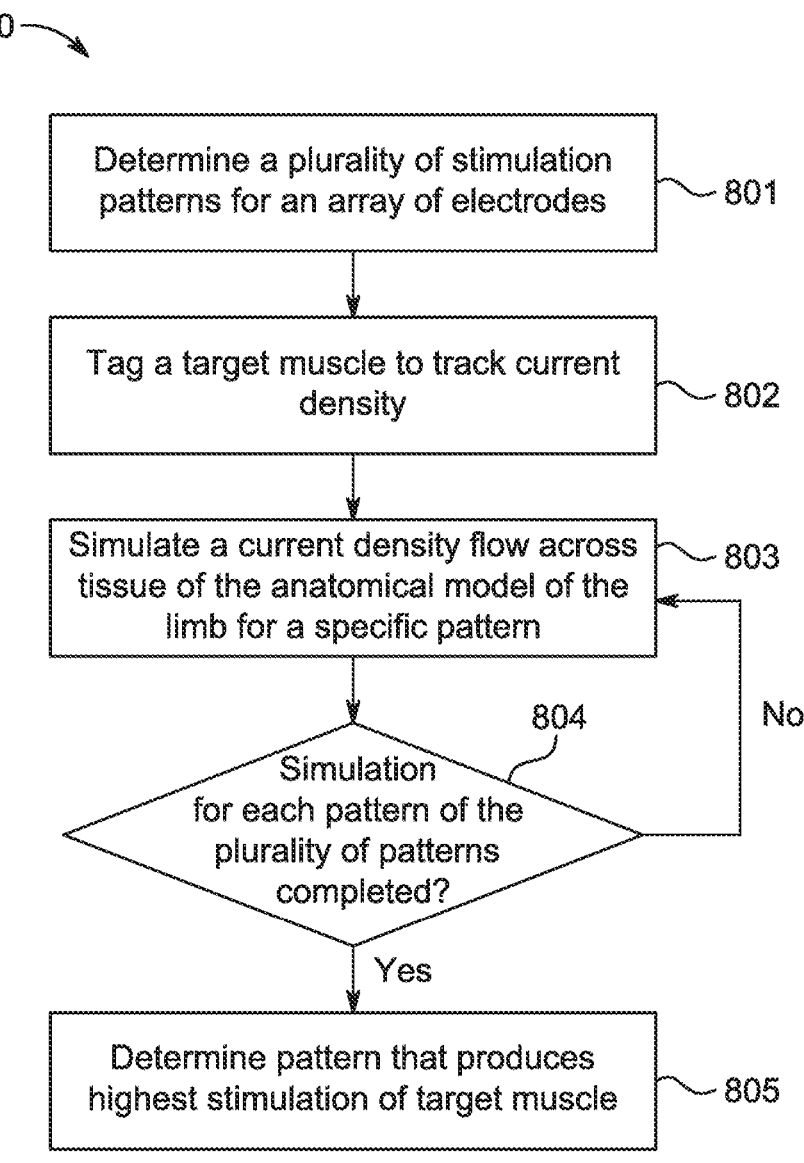
FIG. 8 is a flowchart diagram of a method for determining a pattern for an array of electrodes that produces the highest stimulation of a target muscle, according to an embodiment.

FIG. 8 is a flowchart diagram of a method for determining a pattern for an array of electrodes that produces the highest stimulation of a target muscle 800, in accordance with the embodiments disclosed above. The method of FIG. 8 may be performed by a processor. At 801, a plurality of stimulation patterns for an array of electrodes may be determined. At 802, a target muscle of an anatomical model of a limb is tagged to track current density. In some embodiments, the anatomical model is a FEM, as discussed above. Next, at 803, a current density flow is simulated across the anatomical model for each of the plurality of stimulation patterns. Next, at 804, it is determined whether a stimulation has been completed for each of the plurality of stimulation patterns. If no, then the process returns to step 803, and a current density flow is simulated for a different pattern. If yes, the process proceeds to 805 and the pattern the produces the highest stimulation of the target muscle is determined. The pattern that produces the highest stimulation may be displayed on a display screen, or the like.

In some embodiments, EIT may be used to determine electrode placement/alignment. Methods using EIT to adjust electrode-based recording and/or stimulation calibrations that are dependent on electrode placement are disclosed.

Figure 9:
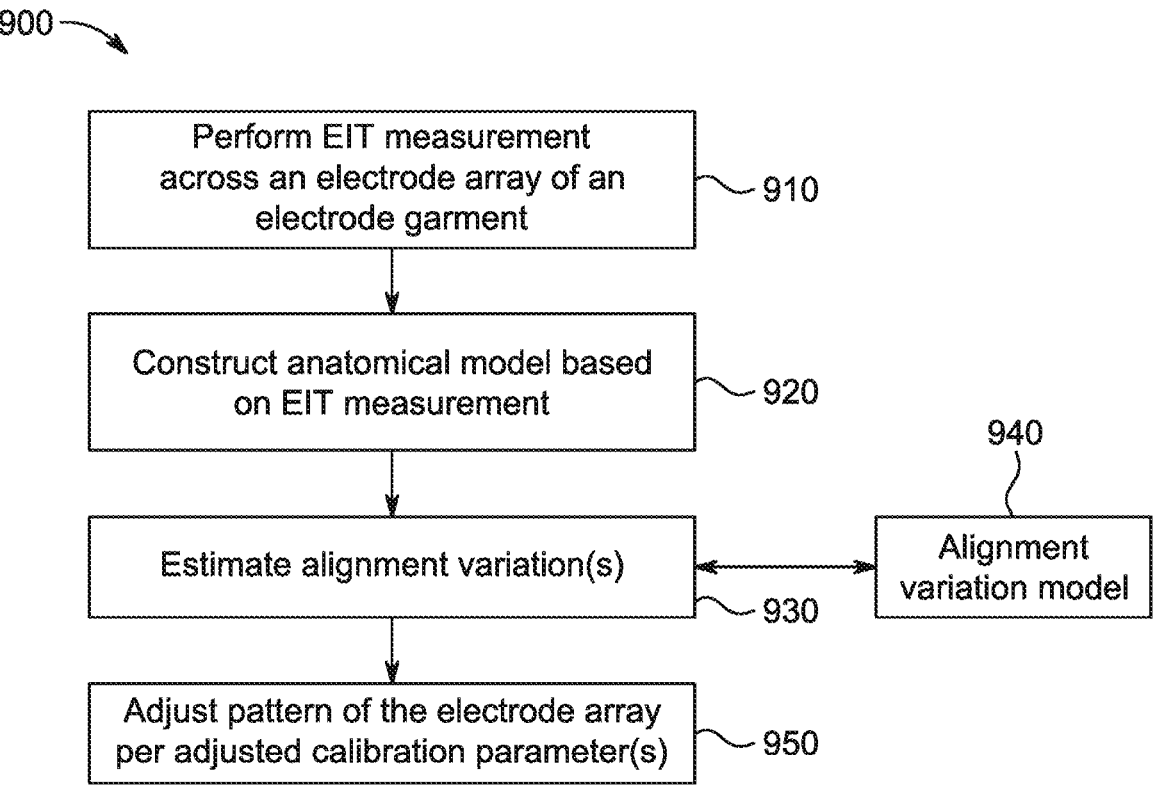
FIG. 9 is a flowchart diagram of a method for using EIT to determine necessary alignment changes following the donning process of an electrode garment 300, according to an embodiment.

FIG. 9 is a flowchart diagram of a method for using EIT to determine necessary alignment changes following the donning process of an electrode garment 900, according to an embodiment. The method of FIG. 9 may be performed by a processor.

At 910, following the donning of an electrode garment, such as a NMES/EMG sleeve, a rapid EIT measurement will be made across an electrode array of the electrode garment.

At 920, the EIT measurement may be used to generate an anatomical model of a limb of interest and identify locations of rigid anatomical markers, such as bone. In some embodiments, three-dimensional (3D) EIT may be used to construct a 3D anatomical model of the limb of interest.

At 930, one or more alignment variations are estimated. The one or more alignment variations may indicate how much the electrode garment has shifted with respect to a reference alignment. By way of example, it may be determined that a distal shift of "x" mm occurred during the donning process. In some embodiments, the alignment variation may comprise one or more of a distal shift, a proximal shift, and/or a relative electrode distance to muscles in different sized arms.

The alignment variations may be estimated by an alignment variation model 940. The alignment variation model 940 may be based on previously collected data. In some embodiments, the alignment variation model 940 may comprise a shared response model. In other embodiments, the alignment variation model 940 may comprise a domain adaptation model. Both the shared response model and the domain adaption model may comprise two parts. In the first part, the determined electrode alignment is aligned to the reference alignment to determine one or more alignment variation(s). The alignment may comprise learning (i.e., estimating) a transformation function. However, as will be appreciated by one having ordinary skill in the art, the shared response model and the domain adaptation model take different approaches to estimating the transformation function. In the second part, a standard classifier or regression algorithm may be trained using collected alignment variation data.

Machine learning may be utilized to improve the alignment variation model 940 over time. In some embodiments, machine learning models which take input data and output predictions may be used. For example, machine learning techniques including, but not limited to, deep learning model, support vector machine, and linear or logistic regression, may be used. The machine learning may comprise a series of transformations in which the estimated alignment variation(s) are compared to a reference alignment over multiple iterations.

At 950, the original calibration parameters of the array of electrodes are automatically adjusted to new calibration parameters. In some embodiments, the pattern of the electrode array may be adjusted. Adjusting the pattern of the electrode may comprise adjusting one or more active electrodes of the electrode garment. For example, if it was determined that a distal shift of x mm occurred during the donning process, the alignment adjustment function may adjust the electrode pattern such that it shifted distally by x mm. In some embodiments, the one or more original calibration parameters may be adjusted using an alignment adjustment function, discussed in more detail with respect to FIG. 10.

In some embodiments, the method of FIG. 9 further comprises optimizing the electrode current, as disclosed in the co-pending application titled "FUNCTIONAL ELECTRICAL STIMULATION CALIBRATION SYSTEM, DEVICES AND METHODS", which is incorporated by reference as if fully set forth.

Figure 10:
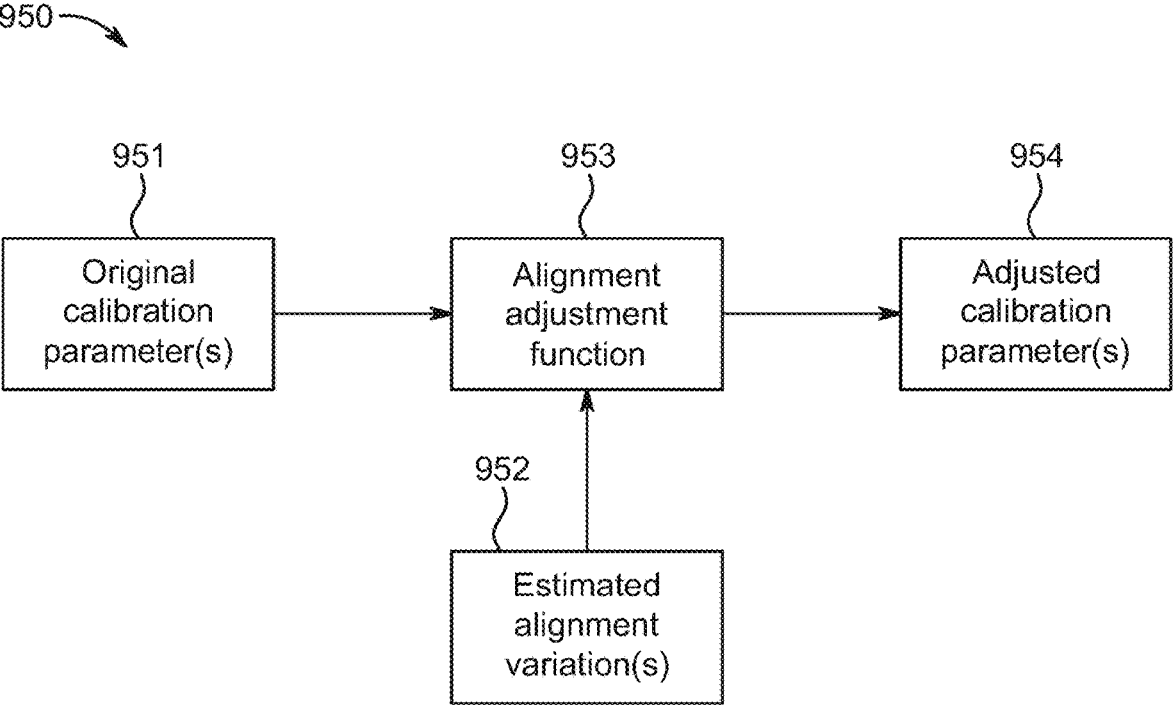
FIG. 10 is a flowchart diagram of a method for adjusting the original calibration parameters to accommodate the determined alignment variations, according to an embodiment.

FIG. 10 is a flowchart diagram of a method for adjusting the original calibration parameters to accommodate the determined alignment variations 950, according to an embodiment. The method of FIG. 10 may be performed by a processor. In some embodiments, the original calibration parameters 951 and the determined alignment variations 952 are input into the alignment adjustment function 953 to determine the adjusted calibration parameters 954. The electrode array of the electrode garment may be automatically adjusted according to the adjusted calibration parameters 954. Therefore, the stimulation pattern in a reference position that generates a desired muscle movement for a reference subject may be adjusted such that it may also generate the desired muscle movement for a new subject.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs).

It will be appreciated that the terminology used in the present application is for the purpose of describing particular embodiments and is not intended to limit the application. The singular forms "a", "the", and "the" may be intended to comprise a plurality of elements. The terms "including" and "comprising" are intended to include a non-exclusive inclusion. Although the present application is described in detail with reference to the foregoing embodiments, it will be appreciated that those foregoing embodiments may be modified, and such modifications do not deviate from the scope of the present application.

What is claimed is:

1. A method for activating electrodes for electrical stimulation, the method comprising:
   generating an anatomical model of a limb based on a medical image of the limb;
   generating a plurality of electrode models on or in the anatomical model of the limb;
   receiving an electrical impedance tomography (EIT) measurement across a physical electrode array positioned on the limb after donning;
   determining, based on the EIT measurement, an electrode alignment relative to the anatomical model and estimating one or more electrode alignment variations using an alignment variation model;
   determining a plurality of candidate patterns for one or more active electrodes of the plurality of electrode models, wherein the candidate patterns are constrained or adjusted based on the estimated one or more electrode alignment variations;
   simulating a current density flow across tissue of the anatomical model of the limb for each candidate pattern of the plurality of candidate patterns while accounting for the estimated one or more electrode alignment variations for the one or more active electrodes; and
   determining the pattern of active electrodes that produces a highest stimulation of a target muscle of the anatomical model of the limb.

2. The method of claim 1, wherein the anatomical model is a finite element model.

3. The method of claim 1, wherein generating the anatomical model of the limb comprises:
   receiving a medical image of the limb;
   isolating materials of the limb into segments;
   specifying values for electrical conductivity of each material; and
   combining the segments together to form an anatomical model.

4. The method of claim 1, wherein specifying one or more active electrodes of the plurality of electrodes comprises:
   specifying one or more electrodes of the plurality of electrodes that generate current; and
   specifying one or more electrodes of the plurality of electrodes that receive current.

5. The method of claim 1, wherein the plurality of candidate patterns of the one or more active electrodes are determined via a numerical optimization algorithm.

6. The method of claim 1, wherein the limb is a forearm.

7. The method of claim 1, further comprising setting a value of a current source.

8. The method of claim 1, wherein electrical stimulation comprises functional electrical stimulation.

9. A system for performing electrical stimulation, the system comprising:
   an electrode array;
   a current source configured to deliver electrical current to the electrode array; and
   a processor configured to:
      generate an anatomical model of a limb based on a medical image of the limb;
      generate a plurality of electrode models on or in the anatomical model of the limb;
      receive an electrical impedance tomography (EIT) measurement across a physical electrode array positioned on the limb after donning;
      determine, based on the EIT measurement, an electrode alignment relative to the anatomical model and estimating one or more electrode alignment variations using an alignment variation model;
      determine a plurality of candidate patterns for one or more active electrodes of the plurality of electrode models, wherein the candidate patterns are constrained or adjusted based on the estimated one or more electrode alignment variations;
      simulate a current density flow across tissue of the anatomical model of the limb for each candidate pattern of the plurality of candidate patterns for the one or more active electrodes; and
      determine the pattern of active electrodes that produces a highest stimulation of a target muscle of the anatomical model of the limb.

10. The system of claim 9, the electrode array is located on an internal surface of a garment.

11. The system of claim 9, wherein the electrode array is configured to perform functional electrical stimulation (FES), electromyography (EMG), or both FES and EMG.

12. A method for calibrating an electrode array, the method comprising:
   receiving an electrical impedance tomography (EIT) measurement across an electrode array;
   generating an anatomical model of a limb and determining an electrode alignment based on the EIT measurement; and
   estimating one or more alignment variations using an alignment variation model.

13. The method of claim 12, wherein the anatomical model is a finite element model.

14. The method of claim 12, further comprising automatically adjusting a pattern of the electrode array to accommodate the one or more alignment variations using an alignment adjustment function.

15. The method of claim 14, wherein automatically adjusting the pattern of the electrode array comprises sending one or more signals to the electrode array to shift a pattern of active electrodes and inactive electrodes.

16. The method of claim 12, wherein the limb is a forearm.

17. The method of claim 12, wherein the electrode array is located on an electrode garment and the method is performed following a donning of the electrode garment.

18. The method of claim 12, wherein the alignment variation model is a shared response model or a domain adaptation model.

19. The method of claim 12, wherein machine learning is used to improve alignment variation model.

20. The method of claim 19, wherein the machine learning comprises a deep learning model, support vector machine, or linear or logical regression.

\* \* \* \* \*